United States Patent [19]

Deacon et al.

[11] Patent Number: 4,925,846
[45] Date of Patent: May 15, 1990

[54] 2-THIAZOLYL-IMIDAZO[1,2,-A]PYRIMI-DINES

[75] Inventors: Robert M. J. Deacon; Roger J. Gillespie, both of Swindon Wilts; Colin R. Gardner, Newbury Berks; Wilfred R. Tully, The Waterloo Cirencester, all of Great Britain

[73] Assignee: Roussel Uclaf, Paris, France

[21] Appl. No.: 57,493

[22] Filed: Jun. 3, 1987

[30] Foreign Application Priority Data

Jun. 4, 1986 [GB] United Kingdom ............... 8613591

[51] Int. Cl.$^5$ .................. A61K 31/505; C07D 487/04
[52] U.S. Cl. .................................. 514/258; 514/257; 544/250; 544/281
[58] Field of Search ............... 544/250, 281; 514/257, 514/258

[56] References Cited

U.S. PATENT DOCUMENTS 4,521,422  6/1985  Dusza et al. ................. 514/258
4,703,049  10/1987  Gillespie et al. .............. 544/281
4,735,957  4/1988  Takaya et al. ................. 544/281

Primary Examiner—Anton H. Sutto
Assistant Examiner—E. Bernhardt
Attorney, Agent, or Firm—Bierman and Muserlian

[57] ABSTRACT

A compound selected from the group consisting of a compound of the formula

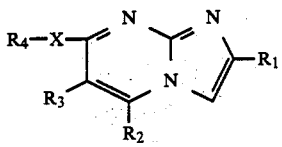

wherein $R_1$ is thiazol-2-yl optionally substituted by 1 or 2 alkyl of 1 to 3 carbon atoms optionally substituted by one or more fluorine or —COOAlk, Alk is alkyl of 1 to 3 carbon atoms, $R_2$ and $R_3$ are individually selected from the group consisting of hydrogen, alkyl of 1 to 3 carbon atoms and alkenyl of 2 to 5 carbon atoms or $R_2$ and $R_3$ together form alkylene of 3 to 5 carbon atoms, X is oxygen or sulfur and $R_4$ is alkyl of 1 to 3 carbon atoms and their non-toxic, pharmaceutically acceptable acid addition salts having minor tranquillizing activity and useful for the treatment of obesity and cognitive impairment.

10 Claims, No Drawings

2-THIAZOLYL-IMIDAZO[1,2,-A]PYRIMIDINES

OBJECTS OF THE INVENTION

It is an object of the invention to provide the novel compounds of formula I and their non-toxic, pharmaceutically acceptable acid addition salts and a process for their preparation.

It is another object of the invention to provide novel compositions and a novel method for the treatment of anxiety, obesity and cognitive impairment.

These and other objects and advantages of the invention will become obvious from the following detailed description.

THE INVENTION

The novel compounds of the invention are selected from the group consisting of a compound of the formula

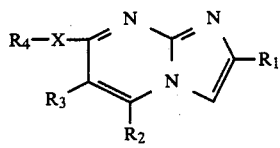

wherein $R_1$ is thiazol-2-yl optionally substituted by 1 or 2 alkyl of 1 to 3 carbon atoms optionally substituted by one or more fluorine or —COOAlk, Alk is alkyl of 1 to 3 carbon atoms, $R_2$ and $R_3$ are individually selected from the group consisting of hydrogen, alkyl of 1 to 3 carbon atoms and alkenyl of 2 to 5 carbon atoms or $R_2$ and $R_3$ together form alkylene of 3 to 5 carbon atoms, X is oxygen or sulfur and $R_4$ is alkyl of 1 to 3 carbon atoms and their non-toxic, pharmaceutically acceptable acid addition salts.

Examples of alkyl of 1 to 3 carbon atoms are methyl, ethyl, n-propyl and isopropyl and examples of alkyl substituted with at least one fluorine atom are trifluoromethyl, difluoromethyl and fluoromethyl. Examples of alkenyl of 2 to 5 carbon atoms are vinyl, allyl or butenyl. Examples of alkylene of 3 to 5 carbon atoms are propylene, butylene and pentamethylene.

Examples of suitable acids to form the non-toxic, pharmaceutically acceptable acid addition salts are inorganic acids such as hydrochloric acid, hydrobromic acid, hydroiodic acid, nitric acid, sulfuric acid and phosphoric acid and organic acids such as formic acid, acetic acid, propionic acid, maleic acid, fumaric acid, succinic acid, tartaric acid, oxalic acid, citric acid, glyoxylic acid and aspartic acid, arylcarboxylic acids such as benzoic acid, alkane sulfonic acids such as methanesulfonic acid and arylsulfonic acids such as benzenesulfonic acid.

Among the preferred compounds of formula I are those wherein $R_1$ is thiazol-2-yl, 4-methylthiazol-2-yl, 4,5-dimethylthiazol-2-yl, 4-ethylthiazol-2-yl, 4-trifluoromethylthiazol-2-yl or 4-ethoxycarbonylthiazol-2-yl, those wherein $R_2$ and $R_3$ are individually alkyl of 1 to 3 carbon atoms or allyl or together form —(CH$_2$)$_4$— and those wherein X is oxygen and their non-toxic, pharmaceutically acceptable acid addition salts.

Specific preferred compounds of the invention are 6-ethyl-7-methoxy-5-methyl-2-(thiazol-2-yl)-imidazo[1,2-a]pyrimidine and 6-ethyl-7-methoxy-5-methyl-2-(4-methylthiazol-2-yl)-imidazo[1,2-a]pyrimidine and their non-toxic, pharmaceutically acceptable acid addition salts.

The novel process of the invention for the preparation of the compounds of formula I comprises reacting a compound of the formula

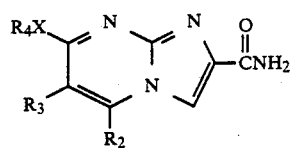

wherein $R_2$, $R_3$, X and $R_4$ have the above definitions with a compound of the formula

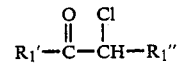

wherein $R_1'$ and $R_1''$ are individually selected from the group consisting of hydrogen and alkyl of 1 to 3 carbon atoms optionally substituted with —COOAlk or at least one fluorine atom, Alk is alkyl of 1 to 3 carbon atoms to obtain the compound of formula I. The reaction is preferably effected in an organic solvent such as ethanol.

When the 4-substituent of the thiazole ring is strongly electron-withdrawing (i.e. —CF$_3$), the intermediate formed with dehydrate to the corresponding thiazole under strongly dehydrating conditions and is preferably subjected to a strong dehydrating agent such as trifluoroacetic anhydride in the presence of a base such as triethylamine in an anhydrous, non-protic solvent such as dichloromethane.

When the 4-position of the thiazole ring is unsubstituted, the dialkylacetal of the haloaldehyde is used rather than the haloaldehyde per se and an aqueous acid is added to the reaction media to ensure "in situ" hydrolysis of the acetal.

The compounds of formula VI may be prepared by reacting a compound of the formula

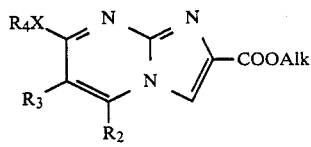

wherein $R_2$, $R_3$, $R_4$ Alk and X have the above definitions with a basic reagent and then an acid agent to obtain a compound of the formula

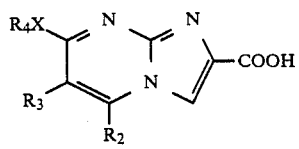

reacting the latter with N,N'-carbonyldiimidazole to obtain a compound of the formula

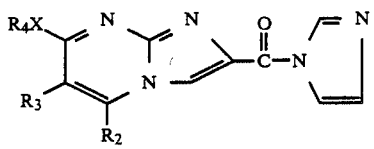

reacting the latter with gaseous ammonia to obtain a compound of the formula

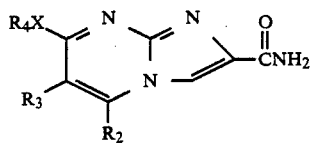

and reacting the latter with Lawesson's Reagent which is 2,4-bis-(4-methoxyphenyl)-1,3-dithia-2,4-diphosphetane-2,4-disulfide to obtain the corresponding compound of formula VI.

In a preferred mode of the process, the compound of formula II is reacted with potassium carbonate in the presence of aqueous methanol and the mixture is heated to reflux, the reaction of the compound of formula III is effected in an organic solvent such as anhydrous dimethylformamide, the reaction of the formula IV with gaseous ammonia is effected in a solvent such as chloroform and the reaction of the compound of formula V with Lawesson's Reagent is effected in an organic solvent such as tetrahydrofuran.

The acid addition salts of the compounds of formula I may be prepared by reacting the compound of formula I with an approximately stoichiometric amount of the acid in solution in a solvent with or without previous isolation of the compound of formula I. The compounds of formula I or their acid addition salts may be isolated and purified by flash chromatography and/or crystallization or any other suitable method.

The compositions of the invention for the treatment of anxiety, obesity and cognitive impairment are comprised of an amount of at least one compound of formula I and their non-toxic, pharmaceutically acceptable acid addition salts sufficient to treat anxiety, obesity and cognitive impairment and an inert pharmaceutical carrier or excipient. The compositions may be in the form of tablets, dragees, capsules, granules, suppositories and injectable solutions or suspensions.

Examples of suitable excipients are talc, gum arahbic, lactose, starch, magnesium stearate, cocoa butter, aqueous and non-aqueous vehicles, animal and vegetable fats, paraffinic derivatives, glycols, various wetting agents, dispersants and emulsifiers and preservatives.

The compositions interact with benzodiazepine receptors in the brain and therefore are useful as minor tranquillizers, as benzodiazepine inverse agonists or antagonists and for the treatment of anxiety, obesity and cognitive dysfunction or cognitive impairment.

The novel method of the invention for treating anxiety, obesity and cognitive impairment in warm-blooded animals, including humans, comprises administering to warm-blooded animals an amount of at least one compound of formula I and their non-toxic, pharmaceutically acceptable acid addition salts sufficient to treat anxiety, obesity and cognitive impairment. The compounds may be administered orally, rectally, or parenterally and the usual daily dose is 1.5 μg/kg to 2.75 mg/kg depending on the condition treated, the method of administration and the specific compound.

The compounds of formula II may be prepared by the process of British Patent No. 2,128,989, for instance.

In the following examples there are described several preferred embodiments to illustrate the invention. However, it is to be understood that the invention is not intended to be limited to the specific embodiments.

EXAMPLE 1

6-Ethyl-7-methoxy-5-methyl-2-(4-methylthiazol-2-yl)-imidazo[1,2-a]pyrimidine

STEP A:

6-Ethyl-7-methoxy-5-methylimidazo[1,2-a]pyrimidine-2-carboxamide

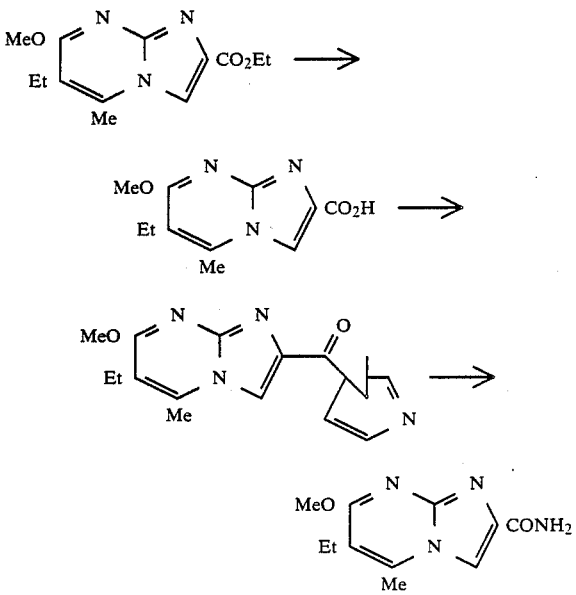

A mixture of 120 g (0.456 mmol) of ethyl 6-ethyl-7-methoxy-5-methylimidazo[1,2-a]pyrimidine-2-carboxylate and 120 g of potassium carbonate in 1200 ml of methanol and 600 ml of water was heated at reflux for 2 hours and the methanol was then evaporated. 150 ml of more water were added, and the resulting solution was acidified to a pH of 1 with concentrated HCl. The solid obtained was filtered and was washed with water, then dried under vacuum over $P_2O_5$ at 80° C. to obtain 87.43 g (82% yield) of 6-ethyl-7-methoxy-5-methylimidazo[1,2-a]pyrimidine-2-carboxylic acid.

To a solution of 87.31 g of the above acid in 1000 ml of dry dimethylformamide was added 73.9 g (0.456) mol of N,N'-carbonyldiimidazole. After stirring the reaction mixture at room temperature for 2 hours, the product was filtered and washed with dimethylformamide, then ether to obtain 104.71 g (99% yield) of 6-ethyl-7-methoxy-5-methylimidazol[1,2-a]pyrimidine-2-carboxyimidazolide.

93.0 g (0.326 mol) of the above imidazolide were dissolved in 1400 ml of chloroform, and ammonia gas was then bubbled through the resulting solution for 2 hours at room temperature. After stirring overnight, the solution was washed 3 times with brine, dried over $MgSO_4$, filtered and evaporated to dryness. The resulting solid was triturated with ether to obtain 68.7 g (90%) of 6-ethyl-7-methoxy-5-methylimidazo[1,2-a]- pyrimidine-2-carboxamide as a white solid melting at 256°–259° C.

STEP B:
6-Ethyl-7-methoxy-5-methylimidazo[1,2-a]pyrimidine-2-thiocarboxamide

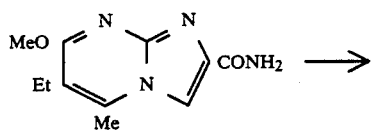

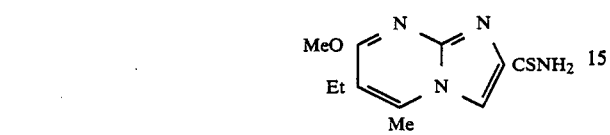

A mixture of 20.0 g (0.0854 mmol) of 6-ethyl-7-methoxy-5-methylimidazo-[1,2-a]pyrimidine-2-carboxamide and 25.4 g (0.0629 mmol) of Lawesson's Reagent in 470 ml of tetrahydrofuran (THF) was refluxed for 4 hours. The mixture was then cooled, and the product was filtered and washed with THF, then ether to obtain 12.06 g (56%) of 6-ethyl-7-methoxy-5-methylimidazo[1,2-a]pyrimidine-2-thiocarboxamide as a yellow solid melting at 248°–259° C.

STEP C:
6-Ethyl-7-methoxy-5-methyl-2-(4-methylthiazol-2-yl)-imidazo[1,2-a]pyrimidine

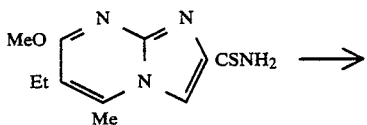

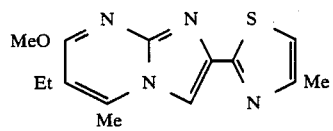

A mixture of 4.30 g (0.017 mol) of 6-ethyl-7-methoxy-5-methylimidazo[1,2-a]pyrimidine-2-thiocarboxamide and 3.18 g (0.0344 mol; 2 eq) of chloroacetone in 300 ml of ethanol was heated under reflux. After 5 hours, 3.18 g of more chloroacetone were added. After 29 hours, the solvent was evaporated, and the residue was dissolved in 2000 ml of water. The solution was made alkaline with concentrated ammonia and was extracted 3 times with chloroform. The chloroform extracts were dried over $MgSO_4$, filtered and evaporated to dryness. The residue was purified by flash chromatography using chloroform as eluent and the resulting solid was recrystallized from ethyl acetate to obtain 3.37 g (68%) of 6-ethyl-7-methoxy-5-methyl-2-(4-methylthiazol-2-yl)-imidazo[1,2-a]pyrimidine as a buff powder melting at 184°–186° C.

EXAMPLES 2 to 10

Using the procedure of Example 1, the compounds of Examples 2 to 10 were prepared.

Example 2: 6-Ethyl-2-(4-ethylthiazol-2-yl)-7-methoxy-5-methylimidazo[1,2-a]pyrimidine Example 3: 2-(4,5-Dimethylthiazol-2-yl)-6-ethyl-7-methoxy-5-methylimidazo[1,2-a]pyrimidine Example 4: Ethyl 2-(6-ethyl-7-methoxy-5-methylimidazo[1,2-a]pyrimidin-2-yl)-thiazole-4-carboxylate Example 5: 6-Ethyl-5-methyl-2-(4-methylthiazol-2-yl)-7-methylthioimidazo[1,2-a]pyrimidine Example 6: 6-Ethyl-7-methoxy-5-methyl-2-(4-trifluoromethylthiazol-2-yl)-imidazol[1,2-a]pyrimidine Example 7: 5-Methoxy-2-(4-methylthiazol-2-yl)-6,7,8,9-tetrahydroimidazo[1,2-a]quinazoline Example 8: 6-Allyl-7-methoxy-5-methyl-2-(4-methylthiazol-2-yl)imidazo[1,2-a]pyrimidine Example 9: 7-Methoxy-5-methyl-2-(4-methylthiazol-2-yl)-6-propylimidazo[1,2-a]pyrimidine Example 10: 6-Ethyl-7-methoxy-5-methyl-2-(thiazol-2-yl)imidazo[1,2-a]pyrimidine Data for the compounds of Examples 1 to 10 are reported in Table I.

EXAMPLE 11

Tablets were prepared containing 20 mg of the compound of Example 1 or 10 and sufficient excipient of lactose, starch, talc and magnesium stearate for a final tablet weight of 150 mg.

PHARMACOLOGICAL DATA

The compounds of formula I are agents which interact with benzodiazepine receptors in the brain, and are useful as minor tranquillizers and for the treatment of obesity or cognitive impairment. Screening for benzodiazepine receptor binding (FRB) was carried out by the method described in published British Patent No. 2,128,989. The values given in Table II are expressed in terms of $IC_{50}$ (nM).

The affinity of the compounds for the benzodiazepine receptor was assessed using the radioligand [$^3$H]-flunitrazepam by modification of the original radioceptor binding method of SQUIRES et al [Nature, (1977), Vol. 266, p. 732]. The values given in Table II below refer to the nanomolar concentration of test compound which inhibited the specific binding of 0.6 nM [$^3$H] flunitrazepam to rat forebrain membrane preparations by 50% ($IC_{50}$ nM).

TABLE I $$R_4X \underset{R_3}{\overset{N}{\underset{\|}{\bigcirc}}} \underset{R_2}{\overset{N}{\bigcirc}} R_1$$

| Example | R₁ | R₂ | R₃ | R₄ | X | Yield(%) | IR(KBr)cm⁻¹ | M.Pt(°C.) | Formula | M.Wt. | Theory/Found C | H | N | S |
|---|---|---|---|---|---|---|---|---|---|---|---|---|---|---|
| 1 | ![S-Me thiazole] | Me | Et | Me | O | 68 | 3085,2975,2950,2920,1640 | 184-186 | C₁₄H₁₆N₄OS | 288.38 | 58.31/58.43 | 5.59/5.59 | 19.43/19.25 | 11.12/11.02 |
| 2 | ![S-Et thiazole] | Me | Et | Me | O | 47 | 3160,2965,1637 | 121-122 | C₁₅H₁₈N₄OS | 302.40 | 59.58/59.54 | 6.00/6.07 | 18.53/18.49 | 10.60/10.58 |
| 3 | ![S-diMe thiazole] | Me | Et | Me | O | 79 | 2970,2920,1630 | 221-222 | C₁₅H₁₈N₄OS | 302.40 | 59.58/59.65 | 6.00/6.01 | 18.53/18.55 | 10.60/10.70 |
| 4 | ![S-CO₂Et thiazole] | Me | Et | Me | O | 60 | 2985,2960,2940,1733,1641 | 211-215 | C₁₆H₁₈N₄O₃S | 346.41 | 55.48/55.54 | 5.24/5.25 | 16.17/16.20 | 9.25/9.26 |
| 5 | ![S-Me thiazole] | Me | Et | Me | S | 64 | 3070,2960,2925,2870,1610 | 151-152 | C₁₄H₁₆N₄S₂ | 304.45 | 55.23/55.06 | 5.30/5.26 | 18.40/18.42 | 21.06/20.92 |
| 6 | ![S-CF₃ thiazole] | Me | Et | Me | O | 80 | 3140,2990,2950,1640 | 179-181 | C₁₄H₁₃N₄OSF₃ | 342.35 | 49.12/49.08 | 3.83/3.80 | 16.37/16.47 | 9.36/9.51 |
| 7 | ![S-Me thiazole] | —CH₂CH₂CH₂CH₂— | | Me | O | 39 | 3060,2935,1640 | 260-263 | C₁₅H₁₆N₄OS | 300.39 | 59.98/59.72 | 5.37/5.38 | 18.65/18.66 | 10.67/10.53 |

TABLE I-continued

| | | | | | | | | | | | Theory/Found | | | |
|---|---|---|---|---|---|---|---|---|---|---|---|---|---|---|
| Example | R₁ | R₂ | R₃ | R₄ | X | Yield(%) | IR(KBr)cm⁻¹ | M.Pt.(°C.) | Formula | M.Wt. | C | H | N | S |
| 8 | (S,N,Me ring) | Me | allyl | Me | O | 76 | 3150,3100,2940,1630 | 149–150 | $C_{15}H_{16}N_4OS$ | 300.39 | 59.98 / 59.91 | 5.37 / 5.38 | 18.65 / 18.73 | 10.67 / 10.60 |
| 9 | (S,N,Me ring) | Me | Pr | Me | O | 71 | 3070,2960,2930,2870,1635 | 160–161 | $C_{15}H_{18}N_4OS$ | 302.40 | 59.58 / 59.56 | 6.00 / 6.00 | 18.53 / 18.67 | 10.60 / 10.57 |
| 10 | (S,N ring) | Me | Et | Me | O | 37 | 2960,2950,2930,1635 | 142–144 | $C_{13}H_{14}N_4OS$ | 274.34 | 56.91 / 56.81 | 5.14 / 5.16 | 20.42 / 20.14 | 11.69 / 11.51 |

TABLE II

| Example | FRB |
|---------|-------|
| 1 | 112 |
| 2 | 220 |
| 3 | 2,500 |
| 4 | 2,800 |
| 5 | 80 |
| 6 | 2,000 |
| 7 | 22 |
| 8 | 100 |
| 9 | 100 |
| 10 | 200 |

Benzodiazepine inverse agonists properties are indicated by the following tests.

(a) Potentiation of threshold seizures induced by audiogenic stimulation in DBA$_2$ mice [Jensen et al—Life Sciences 33, 393–9 (1983)], DBA$_2$ mice are subjected to audio stimulation. The threshold seizure characteristics (myoclonus, running) are potentiated by active compounds to full tonic seizures and ED$_{50}$ is calculated.

Compound of Example 1: ED$_{50}$ 3 mg/kg i.p. (30 mins pretest)

(b) Potentiation of seizures induced by subcutaneous injection of leptazol to CD$_1$ mice.

A dose of leptazol is selected to give 10 to 20% tonic seizures in untreated CD$_1$ mice. Active compounds increase the percentage of tonic seizures and the ED$_{50}$ is calculated by the method of Lichfield and Wilcoxon (J. Pharmacol Exp. Ther. (1949) 96, 99).

Compound of Example 1: ED$_{50}$=50 mg/kg i.p. (30 mins pretest)

(c) Introduction of suprahyoid muscle twitching in urethane anaesthetised Wistar rats [James & Gardner—Europ. J. Pharmacol. 113, 223–8 (1985)]. Wistar rats pretreated with nialamide are anaesthetised with urethane and the suprahyoid muscles exposed. These muscles spontaneously twitch and active compounds increase the amplitude and/or rate of twitch.

Compound of Example 1: MED=10 mg/kg i.p.

Various modifications of the products and method of the invention may be made without departing from the spirit or scope thereof and it is to be understood that the invention is intended to be limited only as defined in the appended claims.

What is claimed is:

1. A compound selected from the group consisting of a compound of the formula

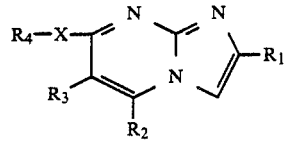

wherein R$_1$ is thiazol-2-yl or thiazol-2-yl substituted by 1 or 2 alkyl of 1 to 3 carbon atoms or alkyl of 1 to 3 carbon atoms subtituted by one or more fluorine or thiazol-2-yl substituted with —COOAlk, Alk is alkyl of 1 to 3 carbon atoms, R$_2$ and R$_3$ are individually selected from the group consisting of hydrogen, alkyl of 1 to 3 carbon atoms and alkenyl of 2 to 5 carbon atoms or R$_2$ and R$_3$ together form alkylene of 3 to 5 carbon atoms, X is oxygen or sulfur and R$_4$ is alkyl of 1 to 3 carbon atoms and their non-toxic, pharmaceutically acceptable acid addition salts.

2. A compound of claim 1 wherein R$_1$ is selected from the group consisting of thiazol-2-yl, 4-methyl-thiazol-2-yl, 4,5-dimethylthiazol-2-yl, 4-ethyl-thiazol-2-yl, 4-trifluoro-methyl-thiazol-2-yl or 4-ethoxy-carbonyl-thiazol-2-yl.

3. A compound of claim 1 wherein R$_2$ and R$_3$ are individually selected from the group consisting of alkyl of 1 to 3 carbon atoms and allyl or together form —(CH$_2$)$_4$— and X is oxygen.

4. A compound of claim 1 selected from the group consisting of 6-ethyl-7-methoxy-5-methyl-2-(4-methyl-thiazol-2-yl)-imidazo[1,2-a]pyrimidine and its non-toxic, pharmaceutically acceptable acid addition salts.

5. A compound of claim 1 selected from the group consisting of 6-ethyl-7-methoxy-5-methyl-2-(thiazol-2-yl)-imidazo[1,2-a]pyrimidine and its non-toxic, pharmaceutically acceptable acid addition salts.

6. A composition for the treatment of cognitive impairment comprising an amount of at least one compound of claim 1 or their non-toxic, pharmaceutically acceptable acid addition salts sufficient to treat cognitive impairment and an inert pharmaceutical carrier.

7. A composition of claim 6 wherein R$_1$ is selected from the group consisting of thiazol-2-yl, 4-methyl-thiazol-2-yl, 4,5-dimethylthiazol-2-yl, 4-ethyl-thiazol-2-yl, 4-trifluoro-methyl-thiazol-2-yl or 4-ethoxy-carbonyl-thiazol-2-yl.

8. A composition of claim 6 wherein R$_2$ and R$_3$ are individually selected from the group consisting of alkyl of 1 to 3 carbon atoms and allyl or together form —(CH$_2$)$_4$— and X is oxygen.

9. A composition of claim 6 wherein the active compound is selected from the group consisting of 6-ethyl-7-methoxy-5-methyl-2-(4-methyl-thiazol-2-yl)-imidazo[1,2-a]pyrimidine and its non-toxic, pharmaceutically acceptable acid addition salts.

10. A composition of claim 6 wherein the active compound is selected from the group consisting of 6-ethyl-7-methoxy-5-methyl-2-(thiazol-2-yl)-imidazo[1,2-a]pyrimidine and its non-toxic, pharmaceutically acceptable acid addition salts.

* * * * *